United States Patent Office

Plant Pat. 1,529
Patented Nov. 20, 1956

1,529

ROSE PLANT

Eugene S. Boerner, Newark, N. Y., assignor, by mesne assignments, to C. W. Stuart & Co., Newark, N. Y., a corporation of New York Application January 4, 1956, Serial No. 557,423

1 Claim. (Cl. 47—61)

The present invention relates to a new and distinct variety of rose plant of the everblooming large-flowered climber class, which was originated by me by crossing the variety "New Dawn" (Plant Patent No. 1) with the variety "Climbing World's Fair" (Plant Patent No. 546).

As the result of this breeding, I have produced a new rose variety which is a truly everblooming climber of the large-flowered class, and which is particularly characterized as to novelty by the following unique combination of outstanding features:

(1) Its continuity of bloom;

(2) Its habit of bearing flowers in large clusters on long, vigorous stems;

(3) The semi-double form of the flowers, and the recurving habit of their center petals, resulting in hiding the stamens and pistils, and thus giving the flowers a double appearance; and (4) The distinctive Tyrian Rose general color tonality of the flowers, and the absence of fading of the color, even in hot weather, until the petals fall.

The foregoing characteristics definitely differentiate my new rose variety from its parents, as well as from all other varieties of its class of which I am aware.

Asexual reproduction of the new variety by both grafting and budding, as performed at Newark, New York, as well as in Arizona and California, shows that the foregoing characteristics and distinctions come true to form and are established and transmitted through succeeding propagations.

The accompanying drawing shows a typical specimen plant of my new variety in its typical flowering stage and as depicted in color as nearly true as it is reasonably possible to make the same in a color illustration of this character.

The following is a detailed description of my new variety. with color terminology in accordance with the Horticultural Color Chart issued by the British Color Council in collaboration with the Royal Horticultural Society, except where general color terms of ordinary dictionary significance are obvious:

Type: Hardy; climbing; outdoor; seedling; for garden decoration.

Class: Hybrid everblooming large-flowered climber.

Breeding: Seedling.

*Seed parent.*—"New Dawn."

*Pollen parent.*—"Climbing World's Fair."

Propagation: Holds its distinguishing characteristics through succeeding propagations by both grafting and budding.

*Flower*

Locality where grown and observed: Newark, New York, Arizona, and California.

Flowers borne: Several to stem; in regular flat clusters; on strong, long stems.

Quantity of bloom: Abundant, outdoors.

Continuity: Continuous.

Fragrance: Moderate in newly opened roses. Nature—ordinary rose fragrance.

Bud:

*Peduncle.*—Medium length; medium caliper; erect; entirely smooth; with numerous red prickles. Color—reddish.

*Before calyx breaks.*—Size—small. Form—ovoid; with foliaceous appendages on the surface of the bud: without foliaceous parts extending beyond the tip of the bud. Color—Sulphur Yellow, Plate 1/1, overlaid with Crimson, Plate 21.

*As first petal opens.*—Size—medium. Form—ovoid. Color: outside—Carmine, Plate 21/1; inside—Carmine, Plate 21/1.

*Opening.*—Opens up well.

Bloom:

*Size (when fully open).*—Medium; from 3½ inches to 3¾ inches.

*Petalage.*—Semi-double; from 15 to 20 petals; center petals recurved and hide the stamens and pistils, thereby giving the flowers a double appearance.

*Form.*—Cupped at first, but becoming very flat; petals being at first loosely rolled inward, but becoming very loosely rolled outward later at maturity.

Petals:

*Texture.*—Leathery. Inside — velvety. Outside — shiny.

*Shape.*—Outside—round oval. Intermediate—round oval. Inside—irregularly scalloped.

This description of a newly opened flower was made from a rose grown outdoors in the month of September, at Newark, New York:

*Color.*—Outer petal: outside surface—Tyrian Rose, Plate 24/1; inside surface—Tyrian Rose, Plate 24. Intermediate petal: outside surface—Tyrian Rose, Plate 24/1; inside surface—Tyrian Rose, Plate 24. Inner petal: outside surface—Tyrian Rose, Plate 24/1; inside surface—Tyrian Rose, Plate 24.

This description was made from a rose that was open for 5 days outdoors in the month of September, at Newark, New York:

*Color.*—Outer petal: outside surface—Tyrian Rose, Plate 24/1; inside surface—Tyrian Rose, Plate 24. Inner petal: outside surface—Tyrian Rose, Plate 24/1; inside surface—Tyrian Rose, Plate 24.

*General color effect.*—Newly opened flower—Tyrian Rose. 3-days open—Tyrian Rose.

*Behavior.*—Drop off cleanly; flowers do not fade; no apparent adverse effect due to weather conditions.

*Flower longevity.*—On bush in garden—5 days in September. Cut roses grown outdoors and kept at living-room temperatures—4 days in September.

*Reproductive organs*

Stamens: Very many; regularly arranged about pistils.

Filaments: Long. Color—Canary Yellow, Plate 2/3.

Anthers: Small; all open at once. Color—Cadmium Orange, Plate 8/1.

Pollen: Moderate. Color—gold.

Pistils: Many.

Styles: Uneven; medium length; medium caliper; separated.

Stigma: Color—yellow.

Ovaries: All enclosed in calyx.

Hips: Globular; smooth; walls thick and fleshy. Color—green.

Sepals: Permanent; medium length; recurved.

Seeds: Many; medium size.

*Plant*

Foliage:

*Leaves.*—Compound of 7 leaflets; normal abundance; medium size; leathery.

*Leaflets.*—Shape—oval. Base — acute. Margin — irregularly serrate.

*Color.*—Mature: upper surface—Spinach Green, Plate 0960/1; under surface—Sage Green, Plate 000861/1. Young: upper surface — Scheeles Green, Plate 860/1, with margins of Chrysanthemum Crimson, Plate 824/1; under surface—Willow Green, Plate 000862/1.

*Rachis (the supporting stem of the compound leaf).*—Medium caliper. Upper side—grooved. Under side—smooth, but sparsely thorny.

*Stipules.*—Attached to the rachis.

*Disease resistance.*—Average resistance to blackspot, as compared with other varieties of the same class grown under comparable cultural conditions at Newark, New York.

Growth:

*Habit.*—Climbing. *Growth.*—Vigorous. *Canes.*—

Heavy. *Main stems.*—Color—green. Thorns—many; medium length; straight; with narrow base. Prickles—none. Hairs—none.

*Branches.*—Color—green. Thorns—many; medium length; straight; with narrow base. Prickles—none. Hairs—none.

*New shoots.*—Color—green. Thorns—many; with narrow base. Prickles—none. Hairs—none.

I claim:

A new and distinct variety of rose plant of the ever-blooming large-flowered climber class, substantially as herein shown and described, characterized particularly as to novelty by its continuity of bloom, its habit of bearing flowers in large clusters on long and vigorous stems, the semi-double form of its flowers in which the central petals are recurved and hide the stamens and pistils and thereby give the flowers a double appearance, and the distinctive Tyrian Rose general color tonality of the flowers which does not fade, even in hot weather, until the petals fall.

No references cited

Nov. 20, 1956 E. S. BOERNER Plant Pat. 1,529
ROSE PLANT
Filed Jan. 4, 1956
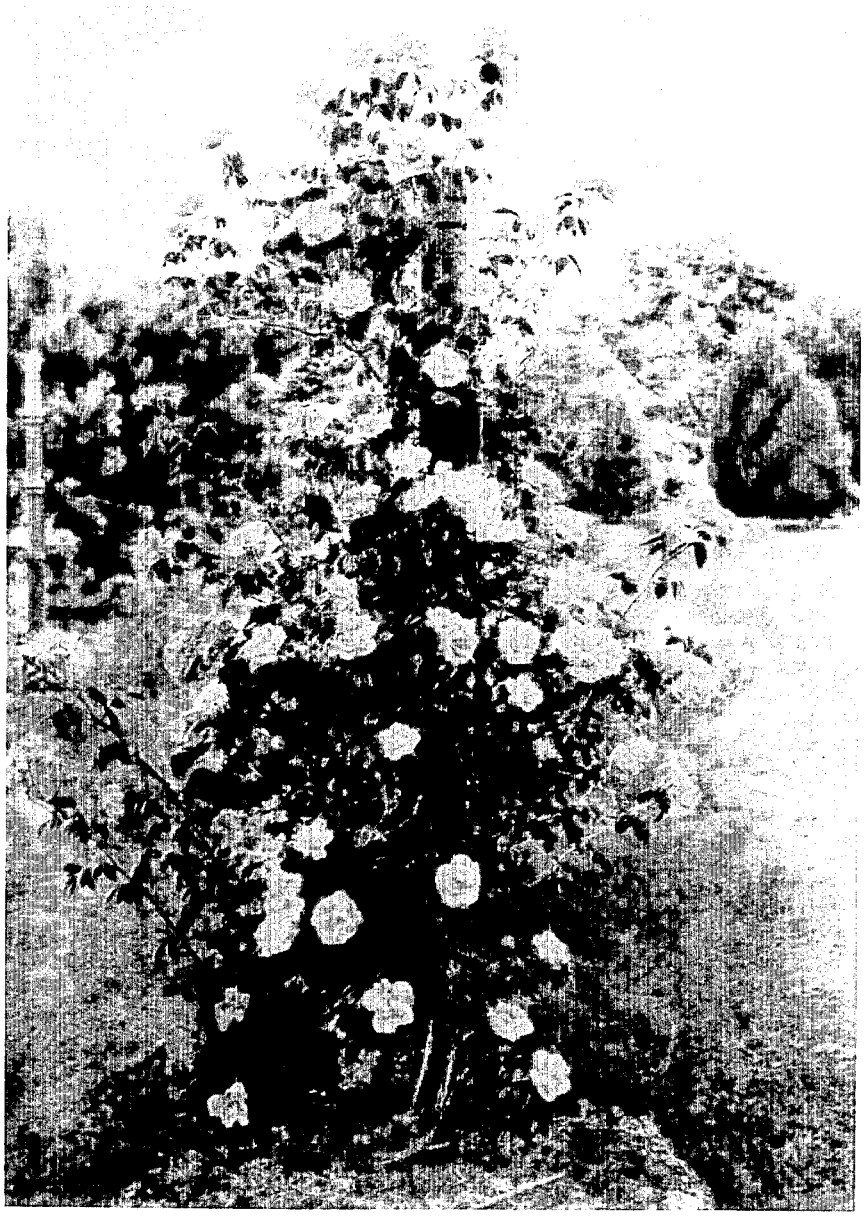
Inventor.
E. S. Boerner
By: Robb & Robb
Attorneys.